United States Patent [19]
Schütz

[11] Patent Number: 5,741,268
[45] Date of Patent: Apr. 21, 1998

[54] TACKING DEVICE AND TACKING NAILS FOR SURGERY

[76] Inventor: Frank-Ullrich Schütz, Anne-Frank-Strasse 33, D-97082 Wurzburg, Germany

[21] Appl. No.: 618,415

[22] Filed: Mar. 15, 1996

[30] Foreign Application Priority Data

Mar. 18, 1995 [DE] Germany ............. 195 09 966.4

[51] Int. Cl.⁶ .................................................. A61B 17/58
[52] U.S. Cl. .............. 606/104; 606/75; 227/146; 227/175.1
[58] Field of Search .................... 606/104, 72, 75, 606/76, 77; 81/23, 20, 27, 473, 474, 448; 227/146, 132, 179.1, 175, 147, 142

[56] References Cited

U.S. PATENT DOCUMENTS

| | | | |
|---|---|---|---|
| 1,601,324 | 9/1926 | Reynolds | 227/132 |
| 2,765,463 | 10/1956 | De Anguera | 227/146 |
| 4,709,765 | 12/1987 | Campanell | 227/146 |
| 4,821,942 | 4/1989 | Richards et al. | 227/132 |
| 4,838,471 | 6/1989 | Chiesa | 227/147 |
| 5,059,206 | 10/1991 | Winters | 606/77 |
| 5,398,861 | 3/1995 | Green | 227/146 |
| 5,544,552 | 8/1996 | Kirsch et al. | 227/147 |

FOREIGN PATENT DOCUMENTS

| | | | |
|---|---|---|---|
| 447828 | 8/1927 | Germany | 227/146 |
| 631842 | 11/1949 | United Kingdom | 227/146 |
| 8504568 | 10/1985 | WIPO | 606/75 |

*Primary Examiner*—Michael Buiz
*Assistant Examiner*—Julian W. Woo
*Attorney, Agent, or Firm*—Edwin D. Schindler

[57] ABSTRACT

A tacking device for surgery, preferably dental surgery, is disclosed for affixing membranes, which are impermeable to tissue cells, with tacking nails to bone. The tacking device has a plunger with an endwise holding device into which a tacking nail, having a head, is able to be inserted. The plunger is movable, directly or by a mechanical transfer element, in the direction of the holding device by a spring force. An untensioning of the spring is blocked by a release device in a releasable manner.

11 Claims, 2 Drawing Sheets

TACKING DEVICE AND TACKING NAILS FOR SURGERY

BACKGROUND OF THE INVENTION

1. Technical Field of the Invention

The invention concerns a tacking device for surgery, preferably for dental surgery, to affix membranes, which are impermeable to tissue cells, with tacking nails to bones, as well as a tacking nail.

2. Description of the Prior Art

For regenerating absent bone tissue methods are known based on the principle of "Guided Tissue Regeneration", which are applied especially in the sector of implantology, as the presence of a sufficient volume of healthy bone tissue is an essential precondition for the stable and durable dwelling of an implant. Especially when dental prostheses are implanted in the jawbone, the situation often arises that there is insufficient bone material to embed the implant and bone must be grown. To this end, bone particles are taken from another place and placed on the bone surface of the region where the new bone tissue is to grow or the underlying bone is drilled to release osteocytes, which effect bone growth, and then a membrane which is impermeable to tissue cells is placed thereupon (Schweiz Monatschrift Zahnmed., Vol. 102, 1992 1491 to 1501). Since the membrane stops soft-tissue cells, which prevent osteogenesis, from penetrating, undisturbed bone growth is possible underneath, although it grows only into the available cavities so that the cover must be sufficiently mechanically stable. In the prior art, the cover is affixed by hanging it upon the prosthesis as well as by screwing it directly to the bone. To this end, a hole is first drilled in the bone, the membrane perforated, the perforation then pierced by means of a screw, and the screw inserted in the pre-drilled hole. Thereupon it is screwed down in the bone material. The most serious disadvantageous of this procedure consists therein that the execution of the individual work steps consumes a considerable amount of time, thereby increasing the physical strain upon the patient. Furthermore, the problem often arises that the membrane is twisted as the screw is screwed down and provides insufficient cover in the region in which the bone is to be grown, endangering the success of the operation. Finally for sufficient frictional connection with the screwdriver, screws with sufficiently large heads must be used, limiting the number of possible tacking places; for example in the state of the art membranes cannot be affixed in the region of the jaw ridge, since with time the screw heads would perforate the mucous membrane here.

SUMMARY OF THE INVENTION

Against this background, the invention has the object of developing a device by means of which a membrane can be affixed in substantially less time to the bone, whereby the number of possible places of affixation is increased and the danger of displacement of the cover during tacking is reduced.

This task is solved according to the invention therein that the tacking device has a plunger with a holding device at the end, into which a tacking nail with head is insertable, the plunger is movable directly or via a mechanical transfer element by means of spring power axially in the direction of the nail holding device and untensioning of the spring is blocked by a releasing device in releasable manner.

The invention proposes to affix the membrane to the bone with tacking nails instead of the previously used screws. For this purpose, the tacking nail with its head is inserted into a holding device, which is disposed at the end of a plunger of the tacking device. The plunger is movable axially in the direction of the nail holding device by spring power. Therefore the power of the spring, whereby both pressure as well as tension springs can be used, can be transferred directly or via a mechanical transfer element, e.g. a lever, to the plunger. Untensioning of the spring is blocked in a releasable manner by means of a releasing device, which can engage with the plunger, transfer element, or the spring itself. A membrane is affixed with the tacking device in that the tacking device, with inserted nail, is placed at the intended place of affixation, aligned in the direction the nail is to be driven and the release device actuated. Through the untensioning of the spring, the plunger is accelerated in the driving direction, until the nail meets the membrane and pierces it with its tip, i.e. pre-perforation of the membrane is unnecessary. Owing to the plunger's momentum, the nail is driven into the bone and affixes the membrane in this way. Depending on the execution of the tacking device, the nail is released during the course of the driving process or is drawn out of the holding device when the tacking device is withdrawn.

With the proposed tacking device a substantially faster affixation of the membrane to the bone is achievable. Many previously required process steps, especially the preliminary drilling of a hole, as well as the perforation of the membrane, are no longer required. Therefore, the strain upon the patient during the course of an operation is substantially reduced and the operation costs lowered. Furthermore, the tacking nail demonstrates more favourable affixation behaviour than a screw, i.e. twisting of the membrane is ruled out with a nail, since it is driven into the bone without rotation. As the head of a nail is not used to transfer torque, in contrast to a screw, it an be designed considerably smaller and flatter so that the possible points of affixation of the membrane are substantially increased spatially and include, for example, the jaw ridge.

In a preferred embodiment of the invention, force is transferred from the spring to the plunger via a striker. This is connected endwise to the spring, disposed collinearly to the plunger axis at a distance to the plunger and is displaceable in its direction. After actuation of the release device, the striker is accelerated in the direction of the plunger, impinges thereupon comparable to a hammer and thus drives the nail into the bone. In addition to a simple and compact structural shape, with this embodiment of the invention, there is especially the advantage that the tacking device is placeable with the tip directly upon the membrane at the point where is to be driven in, thus guaranteeing very accurate positioning of the nail.

Where force is transferred with a striker, a retaining spring is useful to which the plunger is affixed. It guarantees that the location of the plunger is determined before the impact of the striker and that as a consequence there is good control over the driving process. At the same time, the striker is sufficiently movable so that it remains possible to drive in the nail.

Furthermore, it is proposed that the plunger movement is limited endwise by a limit stop. A limit stop on the nail side has, on the one hand, the objective of limiting in a defined way the depth the nail is driven in and, on the other hand, after it is reached, to absorb the residual momentum of the plunger to prevent it from being transferred to the bone. Especially in connection with a plunger retaining spring, a plunger limit stop on the striker side is appropriate, against which it rests where necessary under the influence of the force of the retaining spring, and which determines the starting position of the plunger. The position of the limit stop is preferably adjustable and thus allows the setting of different depths that the nail is driven in.

Furthermore, in a development of the invention, the starting position of the striker or the place of affixation of the moving spring is adjustable. Similar to the limit stop, adjustment can be effected, for example, with the aid of a knurled nut. Adjustability offers the possibility to vary the momentum of the plunger in order to effect adjustments to individually or locally different bone structures or in order to fully drive a still partially projecting nail into the bone with a second impact.

In a suitable embodiment of an adjustable striker, it has an incremental stopping device. The associated release device comprises a bolt, which is movable perpendicular to the striker axis, against which the striker rests under the influence of the moving spring with an opposing surface. Along its axis the striker is provided with a plurality of opposing surfaces of the same type, so that a plurality of incremental possibilities of differing potential energies exist for the striker.

A handle fastened to the striker, which projects from the tacking device, is used to tension the spring. It may be disposed laterally or endwise upon the striker, whereby the latter structural design simplifies the handling of the tacking device when work is done in rather inaccessible regions, for instance in the rear part of the oral cavity.

A preferred tacking nail, to be affixed with the tacking device, has a head of flat design perpendicular to the direction of driving to prevent the affixed membrane from slipping away from the nail over the head. Thereby, thinness of the head allows the nail to be used even in spatially restricted positions, for instance in the region of the jaw ridge. The shaft tapers toward the end so that both piercing of the membrane as well as penetration into the bone are facilitated. Owing to the elasticity of the bone tissue, a shaft provided with barbs guarantees secure and durable retention of the tacking nail.

Upon conclusion of osteogenesis, the membrane and affixation elements are to be removed. For this purpose, it is proposed to bevel the head of the nail in the outer region of its underside with the object of facilitating gripping underneath by pliers or another tool. Especially where nails sit very tightly in the bone, removal is simplified in this way.

Suitable for the material of the nail are elementary or alloyed metals that are tissue-tolerant in order to rule out rejection reactions. In particular, titanium and its alloys are tried and trusted in the surgical sector. Alternatively, materials can be used that are absorbed by the body so that there is no longer the necessity to remove the nail upon completion of osteogenesis.

The nail is retained almost exclusively in the outer, stable bone layer, the cortical substance, while the porous structure of the inner bone is damaged by the nail, without promoting its affixation. Since the thickness of the cortical substance of the human jawbone is some 2 to 5 mm, it is proposed that the shaft length should be in the region of 2 to 3 mm.

Further details, features and advantages of the invention can be taken from the following descriptive part in which a typical embodiment of the invention is explained in greater detail with the aid of the drawing.

BRIEF DESCRIPTION OF THE DRAWING FIGURES

The drawing shows in schematic diagram

FIG. 1 a tacking device according to the invention

FIG. 2 a suitable tacking nail.

DETAILED DESCRIPTION OF THE DRAWING AND PREFERRED EMBODIMENTS

Figure 1:
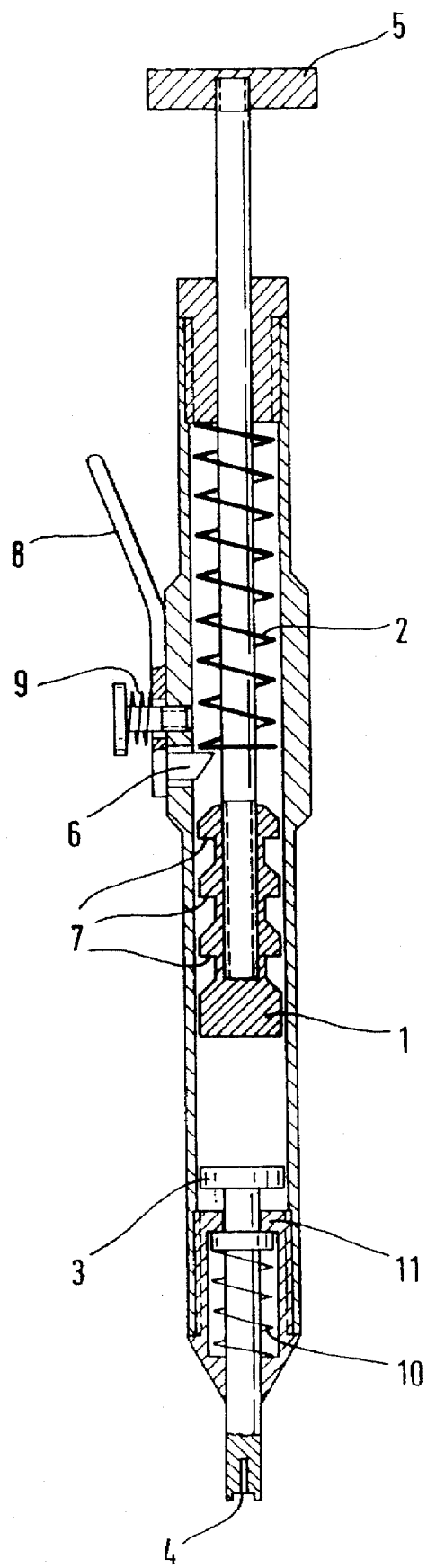

The tacking device shown in FIG. 1 consists in its principal structure of a striker (1), which is moved by the force of a spring (2) against a plunger (3), at the end of which there is a holding device (4), which is designed to receive the head of a tacking nail. Spring (2) is tensioned in that the handle (5), which is connected to striker (1), is pulled out until the bolt (6) engages with an opposing surface (7) of striker (1) and retains it. A plurality of opposing surfaces (7) disposed along the movement axis of striker (1) form a incremental stopping device, which enables spring (2) to be tensioned at differing tensions. The release device of the tacking device is constituted by a lever (8), to which bolt (6) is affixed and which; under the influence of a pullback spring (9), is pressed onto one of opposing surfaces (7).

When lever (8) is actuated, striker (1) is released and moved, by the force of tensioned spring (2), in the direction of plunger (3) upon which impinges in the style of a hammer so that for its part plunger (3) is displaced abruptly in the direction of holding device (4). A nail affixed in holding device (4) is driven in a bone by this plunger movement and thereby can be used to affix a membrane. Plunger (3) is retained by a retaining spring (10)) in the direction toward striker (1) so that for its movement the maximum respective path is available. Limitation of the path length is effected by a limit stop (11), which, after the planned penetration depth is reached, prevents remaining, surplus momentum of the plunger from being transferred to the bone and from causing damage.

Figure 2:
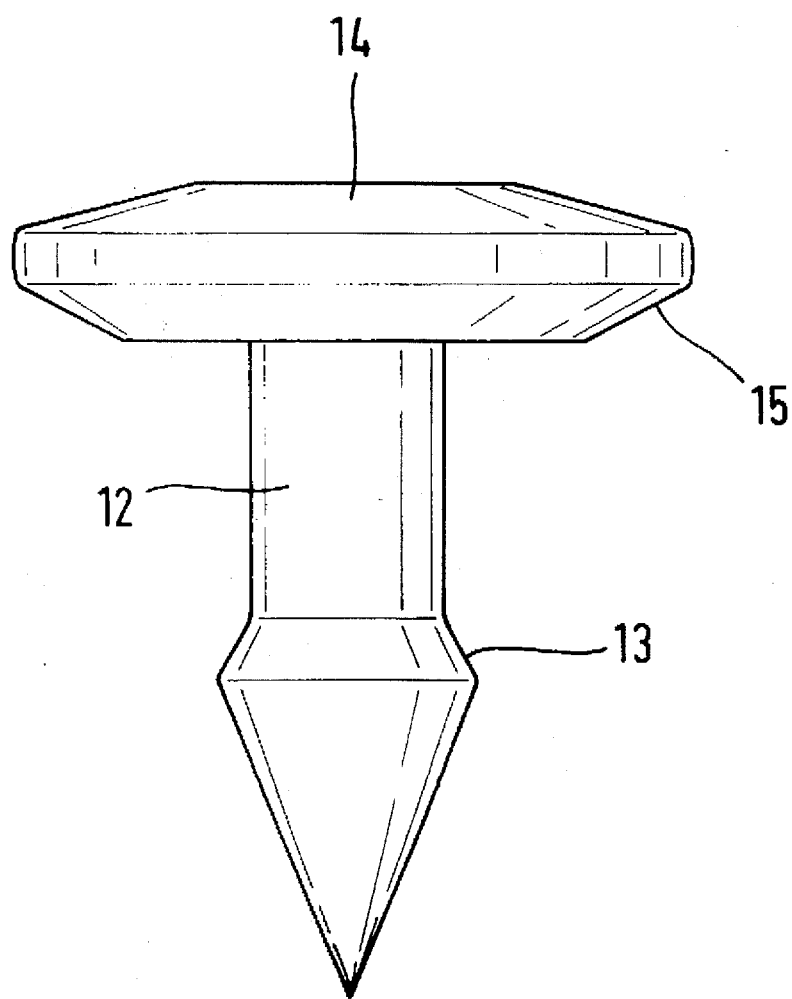

FIG. 2 shows a suitable tacking nail usable in connection with the tacking device. Its shaft (12), the length of which preferably corresponds more or less to the thickness of the cortical substance layer, tapers in a point toward the end in order to facilitate penetration into the bone. Barbs (13) in the region of the shaft ensure secure and durable retention in the bone. The head (14) of the tacking nail is flat in design and thus permits secure affixation of a membrane to the bone, without this being able to slip from shaft (12) away from the nail over head (14). In the outer region of its underside the nail has a bevelment (15), which allows it to be gripped underneath with a toot to remove it together with the membrane after successful bone regeneration.

What is claimed is:

1. A tacking device for surgery, such as dental surgery, for affixing membranes which are impermeable to tissue cells, said tacking device comprising:

a plunger;

a limit stop for limiting endwise movement of said plunger;

a holding device located at one end of said plunger, said holding device being capable of receiving a head portion of a tacking nail;

a striker disposed collinearly to the axis of said plunger, at a distance from said plunger, with said striker being displaceable in the direction of said plunger;

spring means for biassing said striker in the direction of said plunger, said spring means affixed endwise upon said striker; and a releasable means for blocking said spring means from biassing said striker in the direction of said plunger.

2. The tacking device according to claim 1, further comprising a retaining spring, to which said plunger is affixed.

3. The tacking device according to claim 1, wherein said limit stop includes means for adjusting the position of said limit stop.

4. The tacking device according to claim 1, further comprising means for adjusting the affixation of said spring means.

5. The tacking device according to claim 4, wherein said release device is a bolt, which is moveable perpendicularly to an axis of said striker, upon which rests said striker, with one of a plurality of similarly opposing surfaces along its axis.

6. The tacking device according to claim 1, wherein said striker includes a handle which projects over of said tacking device.

7. The tacking device according to claim 1, further comprising a tacking nail drivable into a bone, wherein said tacking nail has a flat structured head, perpendicular to the direction of penetration, and a shaft tapering to a point at an end.

8. The tacking device according to claim 7, wherein said flat structured head is bevelled in an outer region of its underside.

9. The tacking device according to claim 7, wherein said tacking nail is made of a tissue-tolerant, biocompatible metal.

10. The tacking device according to claim 7, wherein said tacking nail is made of an absorbable material.

11. The tacking device according to claim 7, wherein said shaft of said tacking nail has a length of approximately 2–3 mm.

* * * * *